(12) United States Patent
Isozaki et al.

(10) Patent No.: US 7,046,353 B2
(45) Date of Patent: May 16, 2006

(54) SURFACE INSPECTION SYSTEM

(75) Inventors: Hisashi Isozaki, Tokyo-to (JP);
Yoshiyuki Enomoto, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 267 days.

(21) Appl. No.: 10/252,763

(22) Filed: Sep. 23, 2002

(65) Prior Publication Data

US 2003/0103203 A1 Jun. 5, 2003

(30) Foreign Application Priority Data

| Dec. 4, 2001 | (JP) | ........................................ | 2001-370638 |
| Dec. 4, 2001 | (JP) | ........................................ | 2001-370639 |
| Dec. 4, 2001 | (JP) | ........................................ | 2001-370640 |

(51) Int. Cl.
*G01N 21/00* (2006.01)

(52) U.S. Cl. ................................. 356/237.2; 356/237.4

(58) Field of Classification Search ... 356/237.1–237.6; 250/559.1, 559.4, 559.41, 559.44, 559.45
See application file for complete search history.

(56) References Cited

U.S. PATENT DOCUMENTS

| 4,532,723 | A | * | 8/1985 | Kellie et al. | .................... | 356/73 |
| 4,966,457 | A | * | 10/1990 | Hayano et al. | .......... | 356/239.7 |
| 6,122,048 | A | * | 9/2000 | Cochran et al. | ......... | 356/239.4 |
| 6,621,571 | B1 | * | 9/2003 | Maeda et al. | ............. | 356/237.5 |
| 2003/0095251 | A1 | * | 5/2003 | Maeda et al. | ............. | 356/237.2 |

FOREIGN PATENT DOCUMENTS

| JP | 5-273142 | 10/1993 |
| JP | 7-243988 | 9/1995 |
| JP | 9-161304 | 6/1997 |
| JP | 11-160245 | 6/1999 |
| JP | 2001-281162 | 10/2001 |

* cited by examiner

*Primary Examiner*—Michael P. Stafira
(74) *Attorney, Agent, or Firm*—Nields & Lemack

(57) ABSTRACT

A surface inspection system for projecting a laser beam to a surface of a substrate and for detecting a foreign object by detecting scattered reflection light of the laser beam, comprising a light source unit having a plurality of light emitting sources for emitting the laser beams, and a projecting optical system for projecting the laser beam from each of the light emitting sources to the surface of the substrate.

11 Claims, 14 Drawing Sheets

SURFACE INSPECTION SYSTEM

BACKGROUND OF THE INVENTION

The present invention relates to a surface inspection system for inspecting a very small foreign object or a very small flaw such as a crystal defect on a surface of a substrate such as a semiconductor wafer.

A surface inspection system is used for detection of a foreign object or a flaw on a surface of a substrate by projecting a laser beam on the surface of the substrate and by detecting scattered reflection light caused by the foreign object or the flaw. As a light emitting source for the surface inspection system, means such as a gas laser (He, Ar, etc.) has been used in the past. In recent years, a laser diode (LD) is used because of easiness to handle, safety, and longer service life, etc.

FIG. 27 represents a conventional type projecting optical system, using the laser diode as the light emitting source.

A laser beam 2 emitted from a light emitting source 1 is turned to a parallel beam by a collimator lens 3, and the beam is converged to a surface of a substrate 5 such as a wafer (a projecting point 18 at a converging position "f" by an image forming lens 4) by the image forming lens 4. The laser beam 2 is projected to the substrate 5 at an angle of θ. A scattered reflection light detector (not shown) detects a scattered reflection light from a position deviated from a reflection optical axis of the laser beam 2, e.g. from a direction approximately perpendicular to the paper surface. Distribution of a projected light intensity at the projecting point 18 is as shown in FIG. 28.

When the entire surface of the substrate 5 is to be inspected, the projecting point 18 is moved in a radial direction from the center to the outer edge of the substrate at a predetermined speed while the substrate 5 is being rotated. FIG. 28 shows distribution of the projected light intensity of the laser beam 2 at the projecting point 18. It represents a condition where the substrate 5 is rotated by one turn and the projecting point 18 moves from a scanning position "u" to a scanning position "u+1". In this case, the speed of the projecting point 18 in the radial direction is the moving speed over a distance of "p" in the radial direction per one turn of the substrate 5.

Light amount of the scattered reflection light reflected by the foreign object or the flaw is influenced by the projected light intensity of the projected laser beam, and accuracy of detection of the foreign object or the flaw is also influenced by the projected light intensity of the laser beam. Therefore, in order to maintain a predetermined detection accuracy, it is necessary to have the projected light intensity higher than a predetermined light intensity I. The amount of movement "p" per one turn of the substrate as shown in FIG. 28 is determined so that the required projected light intensity I is maintained.

Wavelength of the laser beam 2 projected to the substrate surface is related to detection sensitivity and detection accuracy. By decreasing the wavelength or by increasing the projected light intensity, it is possible to improve the detection sensitivity. Therefore, by widening the range of projection while the projected light intensity is maintained at uniform level, it is possible to increase the detection accuracy while maintaining the detection sensitivity.

For quality control of a product, it is necessary to perform surface inspection of the substrate 5. For instance, in a process to manufacture a semiconductor product, a process of surface inspection for the substrate 5 is incorporated in the manufacturing process.

In recent years, density of semiconductor device is becoming higher, and there have been demands on the more improvement of detection sensitivity and detection accuracy of the surface inspection system. The surface inspection system is required to detect further very small foreign object or flaw on the surface of the wafer. Also, the inspection time required for surface inspection exerts influence on the throughput of the product, and it is desired to carry out the surface inspection quickly.

In the conventional cases as described above, when the projected light intensity of the laser beam is increased, peak value of the projected light intensity distribution is also increased. The detection sensitivity and the detection accuracy is improved by increasing the projected light intensity. In case the increase of the detection accuracy is not required, the amount of the movement for one turn of the substrate, i.e. scanning pitch "p", is increased if the necessary projected light intensity is not changed. As a result, number of turns of the substrate necessary for the scanning of the entire surface of the substrate 5 is decreased, and this leads to the reduction of the time of surface inspection.

However, in case the laser diode is used as the light emitting source, despite of the fact that the laser diode has various advantages such as easiness to handle, safety and longer service life, there is such problem that it has lower light emission amount compared with the gas laser, etc., and there is a limitation to the increase of the projected light intensity. If the projected laser beam has shorter wavelength, the detection accuracy is improved. In this respect, the use of a laser diode emitting a blue laser beam with shorter wavelength is desirable. However, compared with a red laser diode, etc., the blue laser diode has further lower light emission amount, and it has such problem that enough light amount necessary for the surface inspection system can not be provided. To reduce the time for inspection, it is desirable to have wider projection range on the substrate surface. However, if the projection range is widened, the intensity of the projected light beam is decreased, and there has been such problem that both of detection sensitivity and detection accuracy become lower.

As described above, in the surface inspection system, the detection of the foreign object or the flaw is performed based on the detection of scattered reflection light. The scattered reflection light delicately changes according to the property of the substrate surface, i.e. type of film and film thickness. For instance, in case of a silicon oxide film ($SiO_2$) which is formed on the surface of a silicon wafer, it is known that reflectivity changes according to film thickness. Also, it is known that the change of the reflectivity varies periodically according to film thickness, and the changes of the reflectivity is different also according to wavelength of the light.

FIG. 29 shows a reflectivity variation curve corresponding to film thickness for laser beams with 3 different wavelengths (488 nm, 680 nm, and 780 nm) when a silicon oxide film ($SiO_2$) is formed on the surface of the substrate.

The sensitivity to detect the foreign object or the flaw is approximately correlated with reflectivity on the substrate surface. When the reflectivity becomes lower and light amount of the scattered reflection light is decreased, detection accuracy becomes lower. Therefore, in order to maintain a predetermined detection accuracy at a stable level, it is necessary to select the wavelength of the projected laser beam to match the type of film and film thickness.

In the conventional type surface inspection system as described above, it is necessary to set the wavelength of the laser beam to match the type of film and film thickness, and this adversely affects working efficiency. Further, the film thickness is not completely uniform for the entire surface of the substrate, and there is possibility that the reflectivity may vary according to each point of the substrate surface. When the reflectivity varies, there is possibility that the detection accuracy may vary.

SUMMARY OF THE INVENTION

It is an object of the present invention to provide a surface inspection system, by which it is possible to provide sufficient projected light intensity and which contributes to the improvement of inspection accuracy and to the improvement of throughput. It is another object of the present invention to provide a surface inspection system, by which it is possible to perform inspection in stable manner and with high accuracy without being influenced by the type of film or film thickness on the surface of the substrate.

The present invention provides a surface inspection system for projecting a laser beam to a surface of a substrate and for detecting a foreign object by detecting scattered reflection light of the laser beam, comprising a light source unit having a plurality of light emitting sources for emitting the laser beams, and a projecting optical system for projecting the laser beam from each of the light emitting sources to the surface of the substrate. Also, the present invention provides the surface inspection system as described above, wherein the projecting optical system turns the laser beams to parallel beams having optical axes parallel to each other and projects the light beams to the surface of the substrate. Further, the present invention provides the surface inspection system as described above, wherein the projecting optical system comprises an image forming lens, and an optical member arranged to match each of the light emitting sources and for projecting the laser beams from the light emitting sources to the image forming lens. Also, the present invention provides the surface inspection system as described above, wherein optical axes of the light beams entering the image forming lens from the light emitting sources are made parallel to each other. Further, the present invention provides the surface inspection system as described above, wherein optical axes of the light beams entering the image forming lens from the light emitting sources are made parallel to an optical axis of the image forming lens. Also, the present invention provides the surface inspection system as described above, wherein optical axis tilting means for tilting an optical axis is provided on at least one optical axis of the light beams entering the image forming lens from the light emitting sources. Further, the present invention provides the surface inspection system as described above, wherein the laser beam from at least one light emitting source is entered at a predetermined angle with respect to the optical axis of the image forming lens. Also, the present invention provides the surface inspection system as described above, wherein the projecting optical system projects the laser beams from each of the plurality of light emitting sources so that projecting positions on the substrate surface are deviated from each other. Further, the present invention provides the surface inspection system as described above, wherein the projecting optical system has the image forming lens, and optical axis tilting means for tilting an optical axis is provided on at least one optical axis of the light beams entering the image forming lens from the light emitting sources. Also, the present invention provides the surface inspection system as described above, wherein the projecting optical system comprises one image forming lens, and an optical member arranged to match each of the light emitting sources and for entering the laser beam from each of the light emitting sources to the image forming lens, and at least one of the optical axes of the laser beams entering the image forming lens from the light emitting sources is tilted with respect to the optical axis of the image forming lens. Also, the present invention provides the surface inspection system as described above, wherein the projecting positions are deviated in a direction crossing a scanning direction. Further, the present invention provides a surface inspection system for projecting a laser beam to a surface of a substrate and for detecting a foreign object by detecting scattered reflection light of the laser beam, comprising a light source unit having a plurality of light emitting sources for emitting the laser beams, and a projecting optical system for projecting the laser beam from each of the light emitting sources to the surface of the substrate so that reflection characteristics on the substrate surface differ from each other. Also, the present invention provides the surface inspection system as described above, wherein at least one of the plurality of light emitting sources emits a light beam with different wavelength. Further, the present invention provides the surface inspection system as described above, wherein the projecting optical system comprises a polarizing member, and polarizing state of at least one laser beam of the plurality of light emitting sources is changed by the polarizing member. Also, the present invention provides the surface inspection system as described above, wherein the projecting optical system further comprises an image forming lens, and an optical member arranged to match each of the light emitting sources and for entering the laser beam from the light emitting source to the image forming lens. Further, the present invention provides the surface inspection system as described above, wherein the light emitting sources are arranged in form of matrix. Also, the present invention provides the surface inspection system as described above, wherein the plurality of light emitting sources can independently change light emitting condition. Further, the present invention provides the surface inspection system as described above, wherein the optical axis tilting means is a wedge prism. Also, the present invention provides the surface inspection system as described above, wherein the optical axis tilting means is a reflection mirror. Further, the present invention provides the surface inspection system as described above, wherein among the light emitting sources arranged in form of matrix, an optical axis of the laser beam from a light emitting source belonging to a row or a column is tilted. Also, the present invention provides the surface inspection system as described above, wherein each of the plurality of light emitting sources has an optical path independently, and there is provided an optical path switching means on the optical path. Further, the present invention provides the surface inspection system as described above, wherein at least one of arrangement, wavelength, polarization state or light intensity is adjusted in the plurality of the light emitting sources so that a flat reflectivity variation curve can be obtained.

DETAILED DESCRIPTION OF THE PREFERRED EMBODIMENTS

Figure 1:
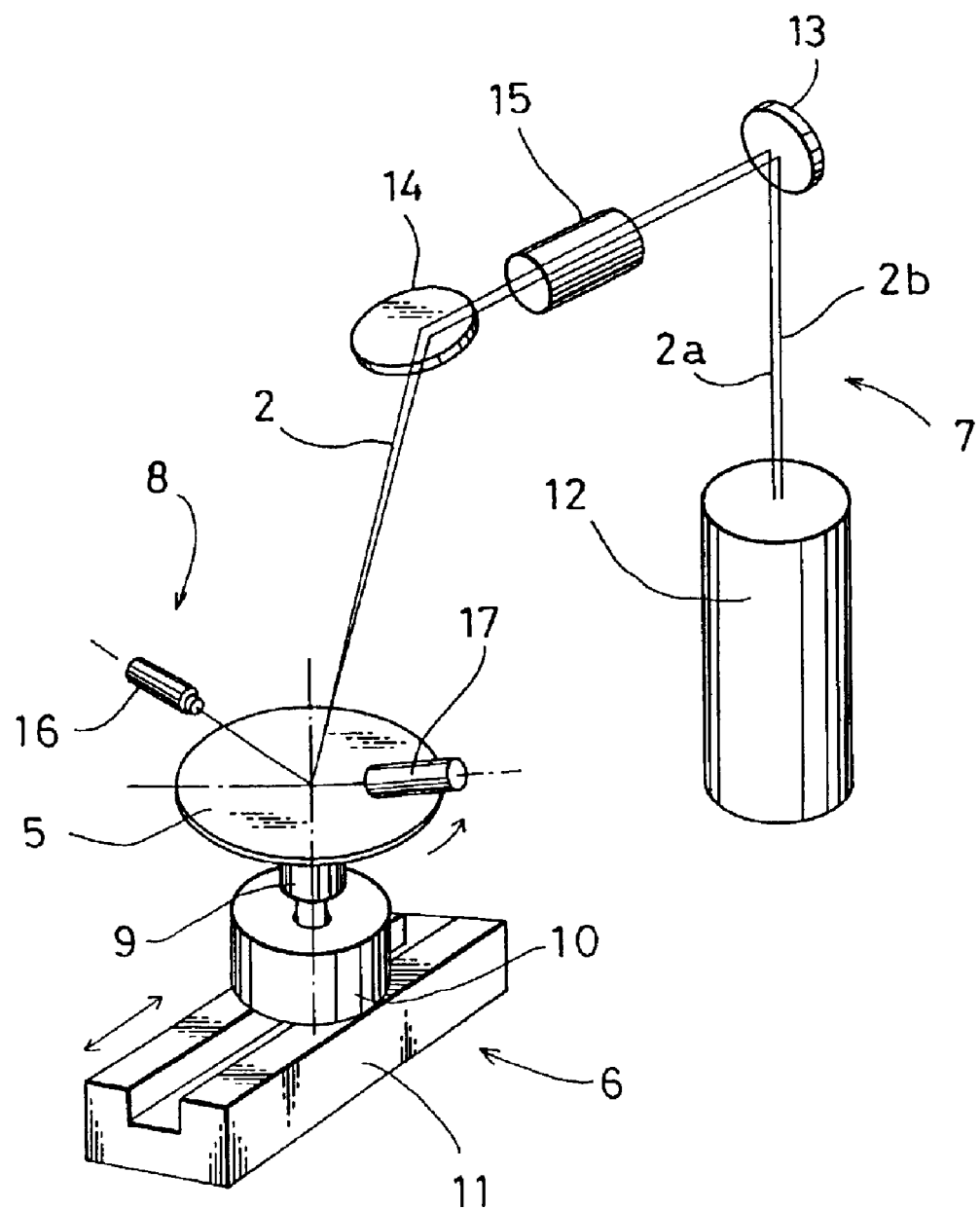
FIG. 1 is a schematical drawing to show a basic arrangement of a surface inspection system according to an embodiment of the present invention.

Description will be given below on embodiments of the present invention referring to the drawings.

First, general features of the surface inspection system will be described referring to FIG. 1.

In the figure, reference numeral 5 denotes a substrate to be inspected such as a wafer. The surface inspection system primarily comprises a scanning drive mechanism 6, a projecting optical system 7, and a detection system 8.

The scanning drive mechanism 6 comprises a substrate holder 9 for holding the substrate 5. The substrate holder 9 is rotatably supported by a rotary drive unit 10. The rotary drive unit 10 is moved linearly in a radial direction in parallel to a rotating surface of the substrate 5 by a linear drive mechanism 11.

The projecting optical system 7 comprises a light source unit 12 for emitting a laser beam 2, serving as an inspection light, deflection optical members 13 and 14 such as mirror for deflecting the laser beam 2 from the light source unit 12 toward the substrate 5, and a lens group 15 for converging the laser beam 2 to the surface of the substrate 5. The detection system 8 comprises photodetectors 16 and 17 having photodetection optical axes, which run perpendicularly to an optical axis of the laser beam 2 projected to the surface of the substrate 5.

In the surface inspection of the substrate 5, the laser beam 2 is projected to the surface of the substrate 5 by the projecting optical system 7 while the substrate 5 is rotated by the rotary drive unit 10, and further the rotary drive unit 10 is moved in the radial direction by the linear drive mechanism 11.

By stepwise movement with a predetermined pitch of each one turn of the substrate 5 or by continuous movement of the rotary drive unit 10 at a predetermined speed, a projecting point 18 of the laser beam 2 is moved from the center toward the outer edge of the substrate 5 along a locus of concentric circles or a spiral circle. As a result, the entire surface of the substrate 5 is scanned by the laser beam 2.

During the process to scan the surface of the substrate 5 by the laser beam 2, if there is a foreign object or a flaw on the surface, the laser beam 2 is reflected by scattering reflection. The scattered reflection light is detected by the photodetectors 16 and 17 of the detection system 8 arranged at predetermined positions. A signal from the photodetectors 16 and 17 is processed by an arithmetic operation unit (not shown), and the foreign object or the flaw can be detected.

Figure 2:
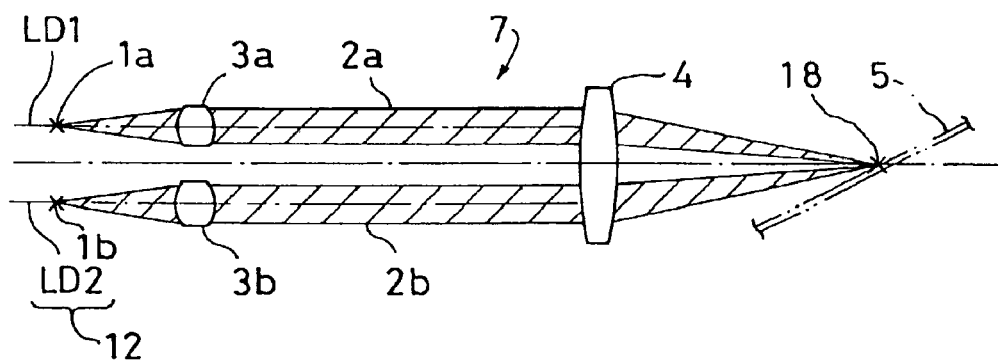
FIG. 2 is a drawing to explain a projecting optical system of the surface inspection system.

FIG. 2 is a schematical drawing to show general features of the surface inspection system of the present invention. Deflection optical members 13 and 14 are not shown in FIG. 2.

The light source unit 12 has two sets of light emitting sources 1a and 1b. Laser beams 2a and 2b coming from the light emitting sources 1a and 1b are turned to parallel beams separately by collimator lenses 3a and 3b and are converged to the surface of the substrate 5 by an image forming lens 4. Optical axes of the collimator lenses 3a and 3b are respectively in parallel to an optical axis of the image forming lens 4 in the basic arrangement, and the laser beams 2a and 2b emitted from the light emitting sources 1a and 1b are converged to the same projecting point 18 by the image forming lens 4.

The light emitting sources 1a and 1b can be independently controlled, and the intensity of the projected light beams of the laser beams 2a and 2b emitted from the light emitting sources 1a and 1b can be changed. The laser beams 2a and 2b may have the same wavelength or may have different wavelength. Because the reflectivity on the surface changes according to wavelength in case the light passes through a transmission film, etc., detection sensitivity is influenced by this change. By having different wavelength, the influence on the wavelength of the reflecting condition on the surface of the substrate 5 can be decreased. The projecting point 18 is positioned on or near a focal plane of the image forming lens 4.

Figure 3:
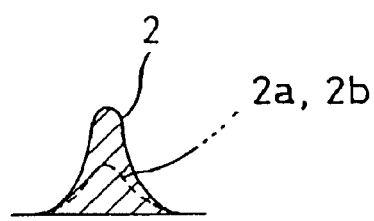
FIG. 3 is a diagram showing light amount distribution at a projecting point in the projecting optical system.

When the laser beams 2a and 2b from the light emitting sources 1a and 1b are converged to the same projecting point 18 by the image forming lens 4, distribution of light amount of the laser beam 2 at the projection point 18 is as shown by a solid line in FIG. 3, and the light amount at the projecting point 18 is increased. In FIG. 3, light amount distribution of each of single laser beams 2a and 2b is shown by a broken line.

Even when the light amount of the emitted light from a single light emitting source is low, the desired projection light intensity can be obtained.

In the above embodiment, two sets of light emitting sources are used, while three sets or more, i.e. a multiple of light emitting sources may be used.

Figure 4:
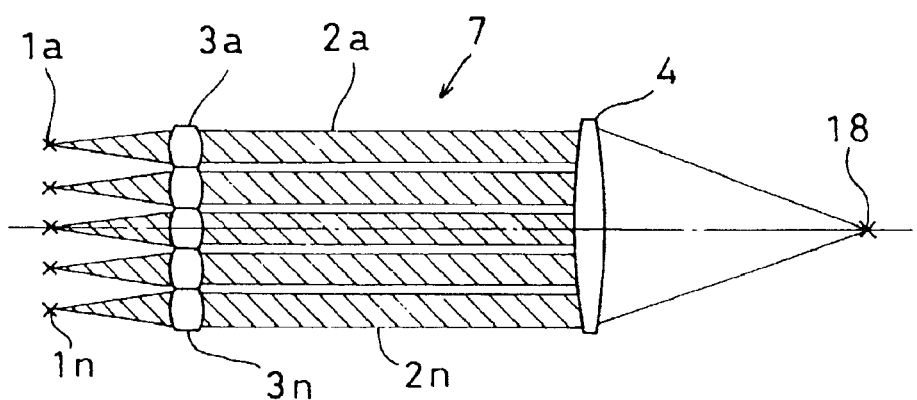
FIG. 4 is a drawing to explain a projecting optical system of a second embodiment of the present invention.

FIG. 4 shows a second embodiment of the present invention where a multiple of light emitting sources 1a, . . . 1n are used.

It is designed in such manner that collimator lenses 3a, . . . 3n are provided to the light emitting sources 1a, . . . 1n respectively so that laser beams 2a, . . . 2n are projected to a single image forming lens 4 via the collimator lenses 3a, . . . 3n respectively. Optical axes of the collimator lenses 3a, . . . 3n are made parallel to an optical axis of the image forming lens 4.

Figure 5:
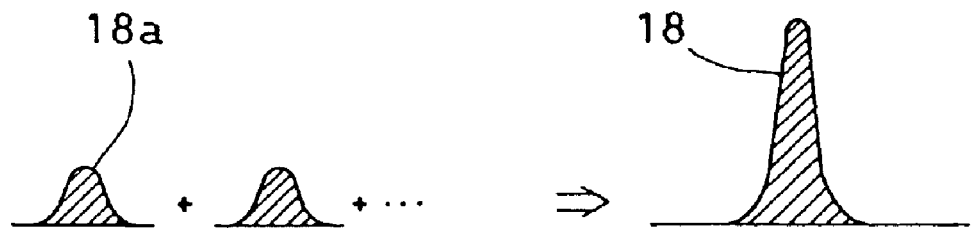
FIG. 5 is a diagram showing light amount distribution at a projecting point in the second embodiment.

In this embodiment, all of the laser beams 2a, . . . 2n are converged to a single projecting point 18. As shown in FIG. 5, the intensity of the projected light at the projecting point 18 is about "n" times as high as the light intensity of a single light emitting source 1. In FIG. 5, light intensity is represented on an axis of ordinate, and space is represented on an axis of abscissa.

In FIG. 4, a plurality of the light emitting sources 1 are arranged in a single column, while these may be arranged in form of matrix containing a plurality of columns.

Because the light source unit 12 has a plurality of light emitting sources 1, distribution of light amount at the projecting point 18 can be adjustable.

Figure 6:
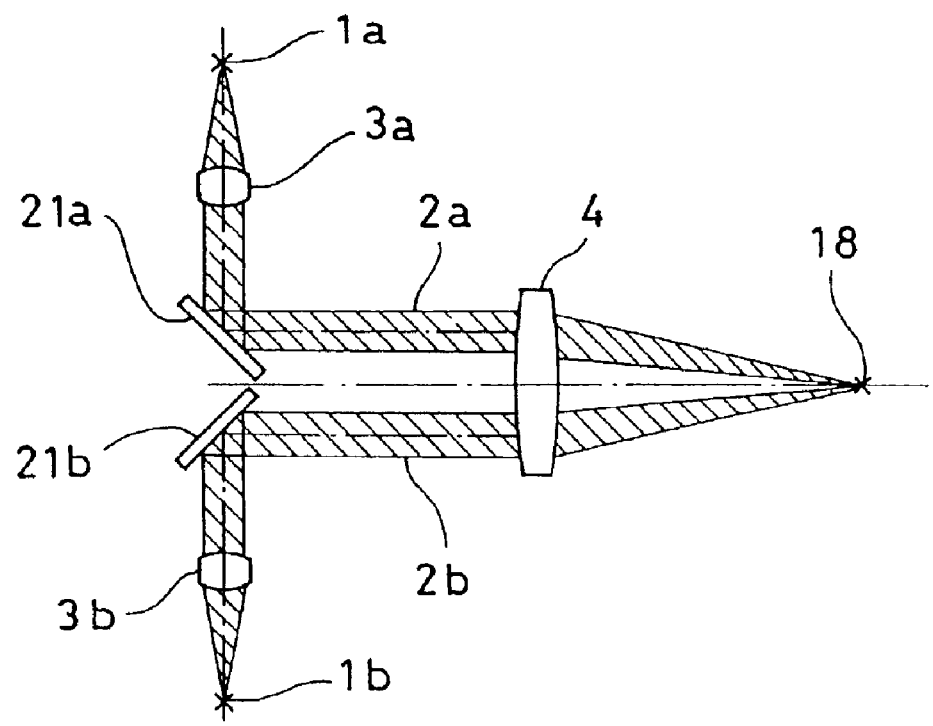
FIG. 6 is a drawing to explain a projecting optical system of a third embodiment of the present invention.

FIG. 6 shows a third embodiment of the invention. In this third embodiment, the light emitting sources 1a and 1b are arranged at positions separated from each other.

The light emitting source 1a and a collimator lens 3a provided to match the light emitting source 1a are arranged at positions crossing with respect to an optical axis of an image forming lens 4, for example, at positions along an optical axis crossing perpendicularly the optical axis of the image forming lens 4. A laser beam 2a emitted from the light emitting source 1a is reflected by a reflection mirror 21a in a direction parallel to the optical axis of the image forming lens 4 and is guided toward the image forming lens 4.

A light emitting source 1b and a collimator lens 3b are also provided in similar arrangement. A laser beam 2b emitted from the light emitting source 1b is reflected by a reflection mirror 21b and is projected in parallel to the optical axis of the image forming lens 4 and enters the image forming lens 4.

The laser beams 2a and 2b emitted from the light emitting sources 1a and 1b are converged to a projecting point 18 by the image forming lens 4.

In case there are three or more light emitting sources 1 in the third embodiment as described above, the light emitting sources 1 and the collimator lenses 3 should be arranged at positions along a radial line having its center on the optical axis of the image forming lens 4.

Figure 7:
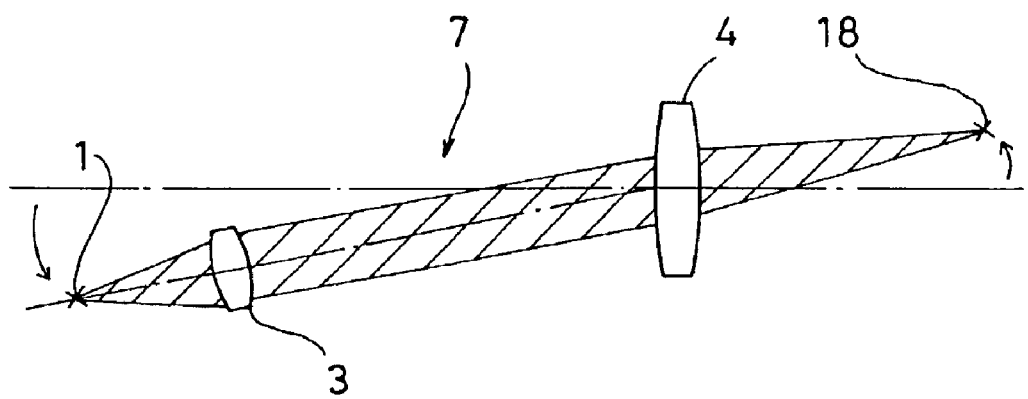
FIG. 7 is a drawing to explain a case where an optical axis is tilted in the projecting optical system of a fourth embodiment of the present invention.

Next, FIG. 7 is a drawing to show a fourth embodiment, in which an optical axis of a collimator lens 3 is tilted with respect to the optical axis of the image forming lens 4.

When the optical axis of the collimator lens 3 is tilted with respect to the optical axis of the image forming lens 4, the projecting point 18 is moved. Therefore, if the optical axis of each of the collimator lenses 3a and 3b is tilted, projecting points 18a and 18b of the light beams from the light emitting sources 1a and 1b are deviated from each other.

Figure 8:
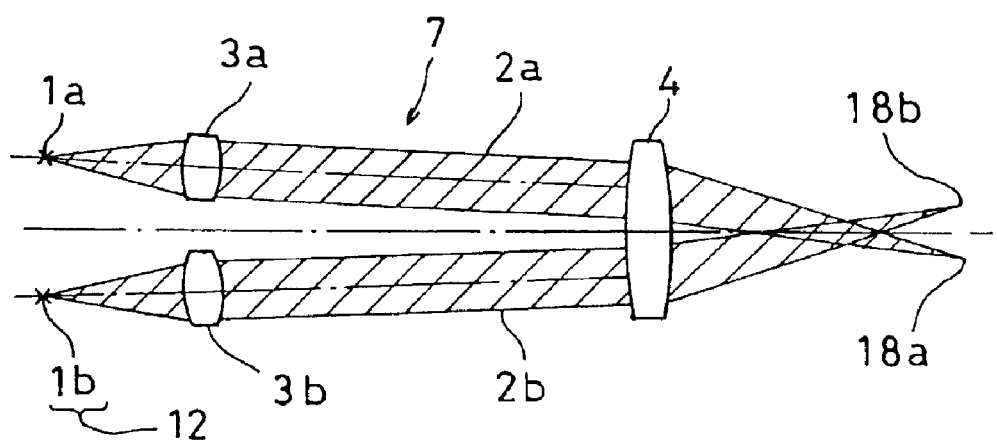
FIG. 8 is another drawing to explain a case where the optical axis is tilted in the projecting optical system of the fourth embodiment of the present invention.
Figure 9:
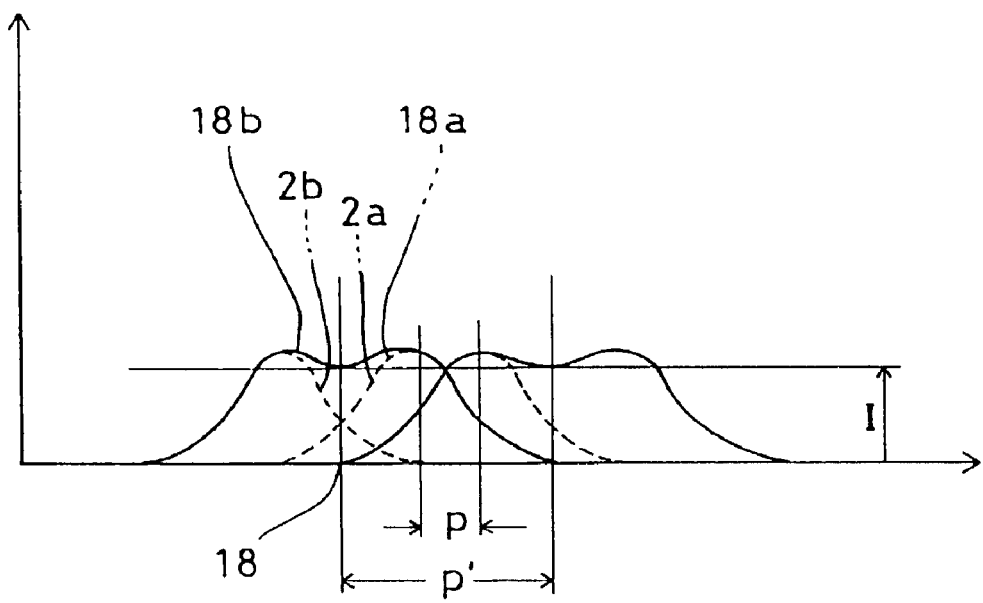
FIG. 9 is a diagram showing distribution of the projected light intensity at a projecting point in the projecting optical system.

The distribution of light intensity of the projected light at the projecting point 18 under the optical conditions shown in FIG. 8 is turned to the synthesized light intensity distribution of the laser beams 2a and 2b shown in FIG. 9, and it is approximately in trapezoidal form as shown by a solid line in the figure. In this case, if it is assumed that the necessary projected light intensity is I and a pitch of scanning is obtained, it is p' as shown in FIG. 9. As reference, the pitch of scanning in case a single laser beam is projected is given by p in FIG. 9.

The direction to synthesize the laser beams is a direction crossing the scanning direction, or more preferably, crossing the scanning direction perpendicularly. That is, a radial direction of the substrate 5 is represented on the axis of abscissa in FIG. 9.

As a result, the range (width) of a predetermined projected light intensity in the projecting point 18 is widened. Thus, it is possible to increase the amount of movement of the projecting point 18 in the radial direction for each rotation during scanning operation. This makes it possible to decrease the number of rotations of the substrate 5 in case of total scanning. Accordingly, the time for surface inspection can be reduced while the detection sensitivity is kept stable.

When the optical axis of the collimator lens 3 is tilted with respect to the optical axis of the image forming lens 4, the optical axis itself of the collimator lens 3 is tilted with respect to the optical axis of the image forming lens 4, while it may be designed in such manner that an optical axis tilting means is provided with respect to the collimator lens 3, and the optical axis of the collimator lens 3 may be tilted with respect to the optical axis of the image forming lens 4 by this optical axis tilting means.

Figure 10:
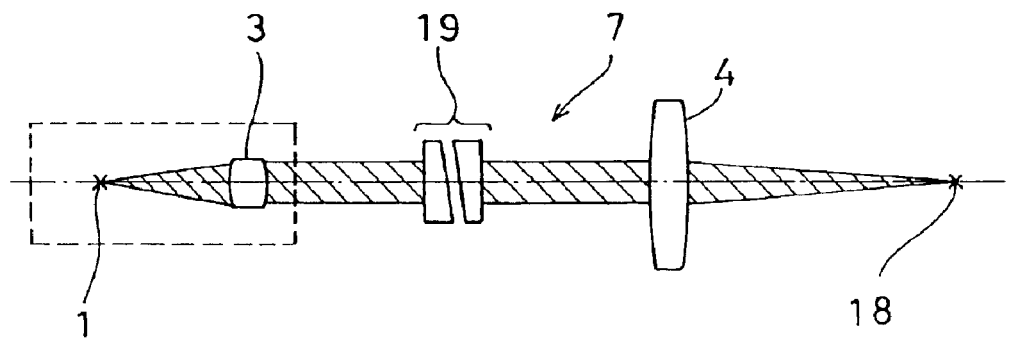
FIG. 10 is a drawing to explain an optical axis tilting means in the projecting optical system.

As the optical axis tilting means for tilting the optical axis of the collimator lens 3, wedge prisms 19 may be placed on the optical axis of the collimator lens 3 as shown in FIG. 10, and the wedge prisms 19 may be rotated in adequate manner. Further, the laser beam 2 emitted from the light emitting source 1 may be guided toward the image forming lens 4 by a deflecting means such as mirror, and the deflecting means may serve as the optical axis tilting means.

Figure 11:
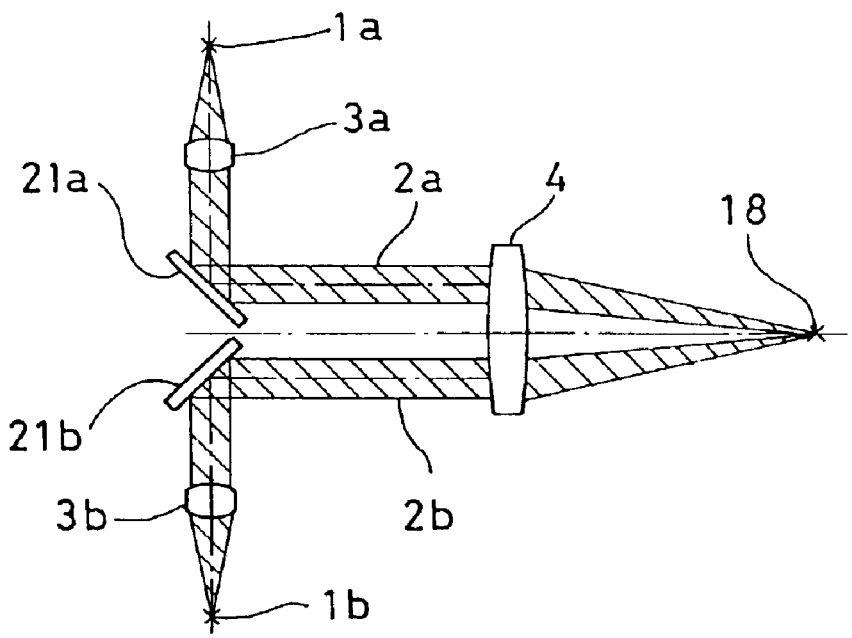
FIG. 11 is a drawing to explain a projecting optical system of a fifth embodiment of the present invention.

FIG. 11 shows a fifth embodiment. A plurality of light emitting sources 1a and 1b and collimator lenses 3a and 3b are arranged on a radial line with its center on the optical axis of the image forming lens 4. Laser beams 2a and 2b are deflected by reflection mirrors 21a and 21b so that the laser beams enter the image forming lens 4. In the projecting optical system shown in FIG. 11, when the reflection mirrors 21a and 21b are tilted, the optical axes of the laser beams 2a and 2b are tilted with respect to the optical axis of the image forming lens 4.

Figure 12:
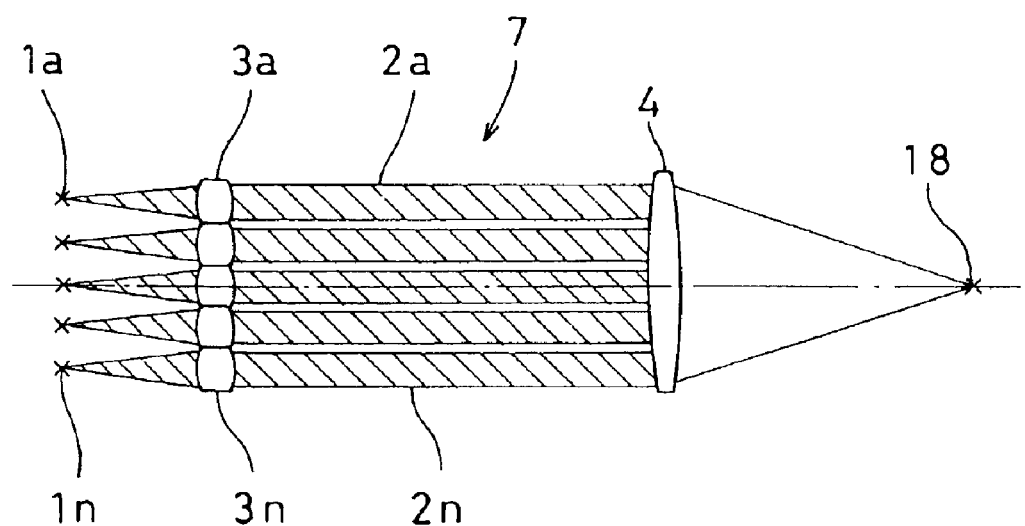
FIG. 12 is a drawing to explain a projecting optical system of a sixth embodiment of the present invention.

FIG. 12 represents a sixth embodiment. A multiple of light emitting sources 1a, . . . 1n are arranged along a straight line, and collimator lenses 3a, . . . 3n are respectively arranged with respect to the light emitting sources 1a, . . . 1n so that laser beams 2a, . . . 2n are projected toward a single image forming lens 4 via the collimator lenses 3a, . . . 3n respectively. As basic arrangement, optical axes of the collimator lenses 3a, . . . 3n are made parallel to the optical axis of the image forming lens 4, and wedge prisms 19 as in FIG. 10 (not shown in FIG. 12) are arranged for each of the optical axes respectively.

Figure 13:
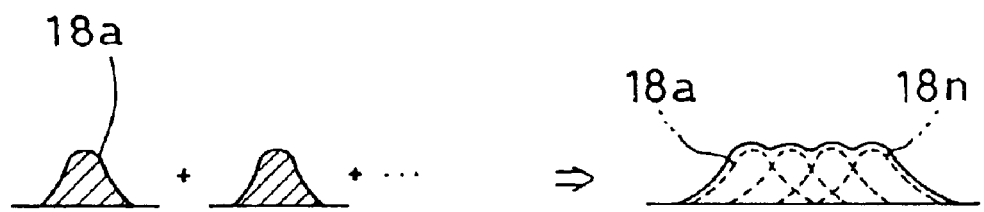
FIG. 13 is a diagram showing distribution of the projected light intensity at a projecting point of the projecting optical system of the sixth embodiment.

The optical axes of the collimator lenses 3a, . . . 3n are tilted more gradually as the optical axes are separated from the optical axis of the image forming lens 4. Then, projecting points 18a, . . . 18n of the laser beams 2a, . . . 2n coming from the light emitting sources 1a, . . . 1n are synthesized being deviated from each other in a radial direction (a direction perpendicular to the scanning direction) of the substrate 5. As a result, the distribution of the projected light intensity in flat trapezoidal form as shown in FIG. 13 is obtained. Therefore, a scanning pitch can be increased further, and number of turns of the substrate 5 necessary for the total scanning can be decreased further.

Figure 14:
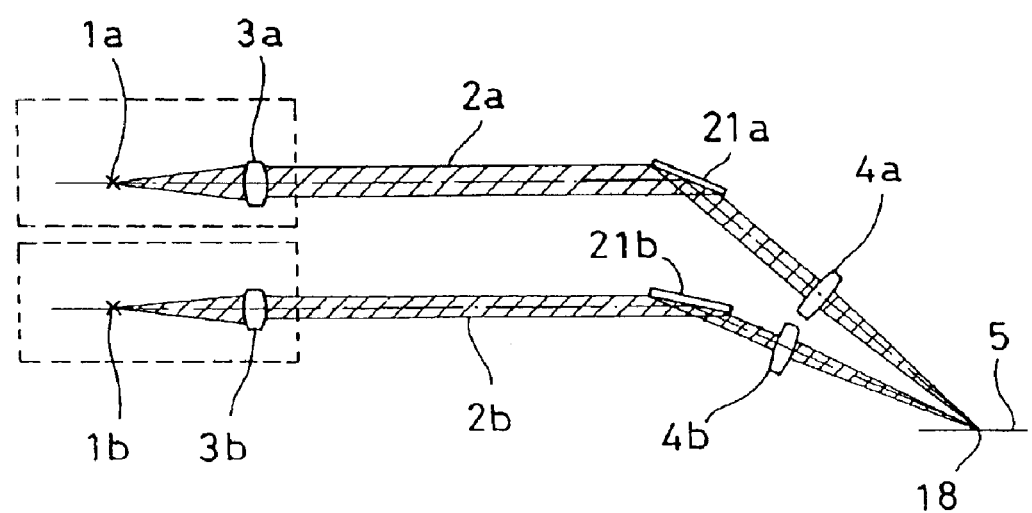
FIG. 14 is a drawing to explain a projecting optical system of a seventh embodiment of the present invention.

In the above embodiment, the laser beams 2a and 2b are projected to the same image forming lens 4. In a seventh embodiment shown in FIG. 14, laser beams 2a and 2b emitted from the light emitting source 1a and 1b are turned to parallel beams by collimator lenses 3a and 3b. Then, the laser beams 2a and 2b are deflected by reflection mirrors 21a and 21b, and the laser beams are converged independently to the same projecting point 18 via the image forming lenses 4a and 4b.

In the projecting optical system as described above, light converting points 18a and 18b of the laser beams 2a and 2b can be deviated in a radial direction of the substrate 5 by the reflection mirrors 21a and 21b, and the projected light intensity distribution as shown in FIG. 9 can be obtained.

Figure 15:
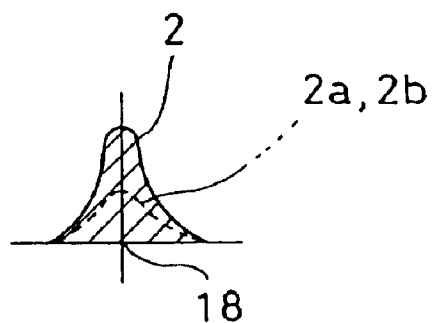
FIG. 15 is a diagram showing distribution of the projected light intensity at a projecting point in case an optical axis is turned to parallel in the projecting optical system shown in FIG. 2.
Figure 16:
FIG. 16 is a diagram showing distribution of the projected light intensity at a projecting point in case an optical axis is turned to parallel in the projecting optical system shown in FIG. 12.

Next, when the light beams of the laser beams 2a and 2b are turned to parallel to the optical axis of the image forming lens 4 in the arrangement of the projecting optical system of FIG. 2, the light beams are converged to the same projecting point 18 as shown in FIG. 15. The projected light intensity distribution is as shown by a solid line in FIG. 15, and the intensity of the projected light is increased by about two times. When all of the optical axes of the laser beams 2a, . . . 2n are turned to parallel to the optical axis of the image forming lens 4 in the arrangement of the projecting optical system of FIG. 12, all of the laser beams 2a, . . . 2n are converged to the same projecting point 18. The distribution of the projected light intensity at the projecting point 18 is a sum of the projected light intensities of the laser beams 2a, . . . 2n as shown in FIG. 16.

Description has been given in FIG. 12 on a case where the light emitting sources 1a, . . . 1n are arranged in one column on a straight line, while it may be designed in such manner that these are further arranged in many columns as desired, and the light emitting sources 1 may be arranged in form of matrix.

When the light emitting sources are arranged in form of matrix, the projected light intensity distribution at the projecting point 18 can be adjusted as given below although it is not particularly shown in the figure.

Figure 17:
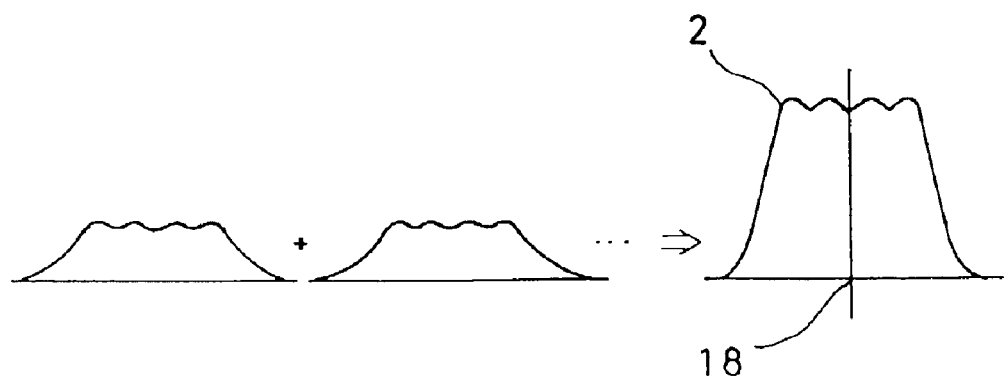
FIG. 17 is a diagram showing distribution of the projected light intensity at a projecting point when light emitting sources are arranged in form of matrix.

That is, optical axes of collimator lenses 3a, . . . 3n are tilted gradually in each column, and optical axes of the collimator lenses 3b, . . . 3m are arranged in parallel in each row. Then, the projected light intensity distribution of flat trapezoidal form shown in FIG. 13 can be obtained for each column. Further, light amount of each of all columns is converged to the same point. As a result, the projected light intensity distribution is overlapped as many times as the number of rows. The projected light intensity distribution shown in FIG. 17 can be obtained, and it is possible to have the laser beams 2 having the projected light intensity as desired and with wide projecting range.

When the projected light intensity is increased, the inspection accuracy can be improved. In this embodiment, it is possible to attain improvement of the inspection accuracy and improvement of the throughput at the same time.

When the plurality of light emitting sources 1 are used and the optical axes of the laser beams 2 are deflected by the optical axis tilting means, it is possible to obtain any projected light intensity distribution as desired and any forms of light beams at the projecting point as desired.

Any projecting conditions can be obtained depending on the circumstances of the surface inspection, i.e. depending on whether preference is given to the throughput or to the increase of accuracy, etc.

As described above, according to a surface inspection system of the present invention, a laser beam is projected to a surface of a substrate, and a foreign object is detected by detecting scattered reflected light of the laser beam, and the surface inspection system comprises a light source unit having a plurality of light emitting sources for emitting the laser beam and a projecting optical system for projecting the laser beam from each of the light emitting sources toward surface of the substrate. The range of projection is widened, which has a predetermined light intensity while maintaining a predetermined projected light intensity. Thus, it is possible to have a scanning step for longer distance and to reduce the time of surface inspection.

There is provided optical axis tilting means for tilting an optical axis on at least one optical axis of the light beams entering an image forming lens from the light emitting sources. Or, the projecting optical system comprises an image forming lens and also comprises an optical member arranged to match each of the light emitting sources and for entering the laser beam from each of the light emitting sources to the image forming lens, and at least one of the optical axes of the light beams entering the image forming lens from the light emitting sources is tilted with respect to the optical axis of the image forming lens. Accordingly, the projected light intensity distribution at the projecting point projected from a plurality of light emitting sources can be adjusted to the light intensity distribution to match the inspecting condition.

Figure 18:
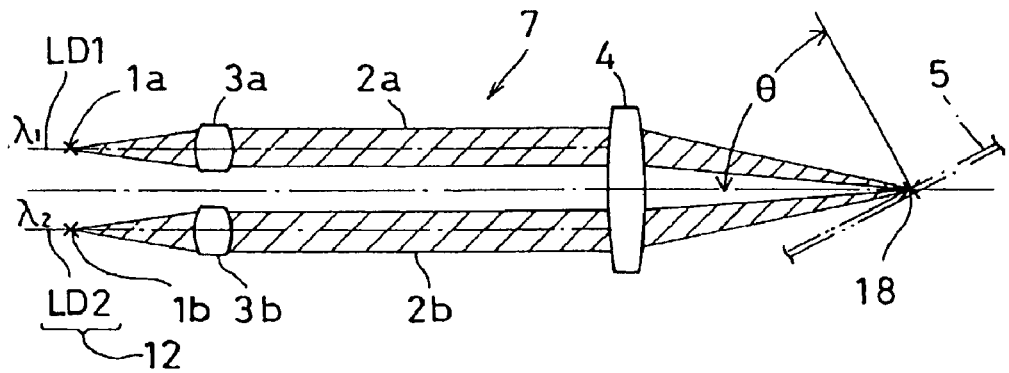
FIG. 18 is a drawing to explain a projecting optical system of a surface inspection system of an eighth embodiment of the present invention.

FIG. 18 is a schematical drawing of a projecting optical system 7 in a surface inspection system of an eighth embodiment of the present invention. In the figure, deflection optical members 13 and 14 are not shown.

The light source unit 12 has two sets of light emitting sources 1a and 1b. The light emitting sources 1a and 1b can independently control light emitting conditions and can emit laser beams 2a and 2b with different wavelengths of λ1 and λ2 respectively.

The laser beams 2a and 2b from the light emitting sources 1a and 1b are independently turned to parallel beams by collimator lenses 3a and 3b respectively and are converged to the surface of the substrate 5 by a single image forming lens 4. Each of optical axes of the collimator lenses 3a and 3b runs in parallel to an optical axis of the image forming lens 4. The laser beams 2a and 2b emitted from the light emitting sources 1a and 1b are converged to the same projecting point 18 via the image forming lens 4.

The laser beams 2a and 2b having different wavelengths from the light emitting sources 1a and 1b are converged and projected to the same projecting point 18 by the image forming lens 4.

Figure 29:
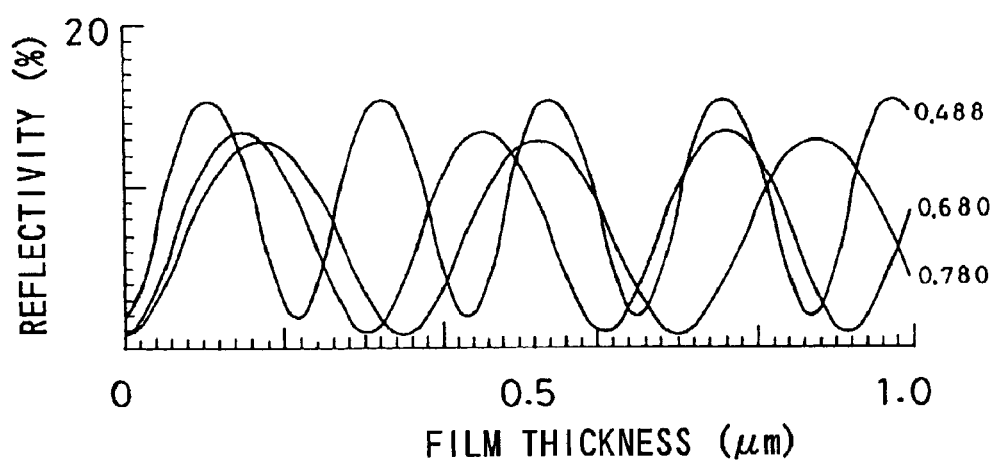
FIG. 29 is a diagram showing the relation between the change of film thickness of the film formed on the substrate surface and reflectivity of laser beams having different wavelengths.

When the single laser beam is projected to the projecting point 18 from each of the light emitting sources 1a and 1b, e.g. when the laser beam 2a with wavelength λ1 is singly projected to the projecting point 18 from the light emitting source 1a, the reflectivity of the scattered reflected light is periodically changed with respect to the change of film thickness just as the predetermined wavelength shown in FIG. 29 in case the film is a silicon oxide film ($SiO_2$) as described above. Although not shown in the figure, in case the laser beam 2b with wavelength λ2 from the light emitting source 1b is singly projected to the projecting point 18, the reflectivity is periodically changed with respect to the change of film thickness in a phase different from the case of the light emitting source 1a just as the different wavelength line shown in FIG. 29.

Next, with regard to the reflectivity, when the laser beams 2a and 2b are projected at the same time from the light emitting sources 1a and 1b, synthesized reflectivity to match the change of film thickness is a synthesized value of the reflectivities of the laser beams 2a and 2b because the phase is deviated as shown in FIG. 29. That is, the reflectivities of the laser beams 2a and 2b are synthesized. As a result, peaks of the reflectivities become almost flat, and reflectivity variation curve is turned to trapezoidal form.

When the laser beams 2a and 2b with two types of wavelengths λ1 and λ2 respectively are projected at the same time to the same projecting point 18, dropping of the reflectivity in predetermined two wavelengths in FIG. 29 can be decreased. Thus, even when the film thickness is changed, the scattered reflection light due to a foreign object or flaw is stabilized, and detection accuracy is kept stable and is not changed.

It may be designed in such manner that the laser beams with three or more different wavelengths may be mixed and are projected to the same projecting point. In this case, the reflectivity variation curve is a synthesis of reflectivities of the laser beams. If such a wavelength is selected that the phase of the reflectivity variation curve of the laser beams is deviated stepwise by adequate amount and if the projected light intensity is adjusted, flat portion of the peaks of the reflectivity variation curve is increased further, and it is more stabilized with respect to the change of film thickness.

Figure 21:
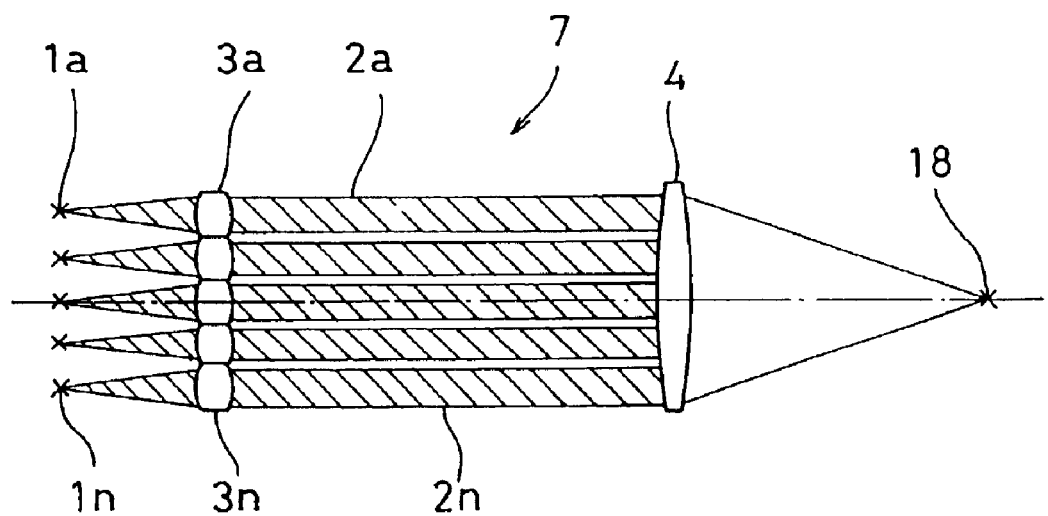
FIG. 21 is a drawing to explain a projecting optical system of a surface inspection system of a ninth embodiment of the present invention.

FIG. 21 shows an example of a projecting optical system where laser beams with three or more different wavelengths are mixed together.

FIG. 21 shows a ninth embodiment. In this embodiment, a multiple of light emitting sources 1a, . . . 1n are used. From the light emitting sources 1a, . . . 1n, laser beams 2a, . . . 2n with different wavelengths respectively are emitted.

The light emitting sources 1a, . . . 1n are arranged in a linear direction, and collimator lenses 3a, . . . 3n are disposed with respect to the light emitting sources 1a, . . . 1n respectively so that the laser beams 2a, . . . 2n are projected to a single image forming lens 4 via the collimator lenses 3a, . . . 3n. Optical axes of the collimator lenses 3a, . . . 3n are made parallel to an optical axis of the image forming lens 4.

In this embodiment, all of the laser beams 2a, . . . 2n having different wavelengths are converged to a projecting point 18. Reflectivities of the laser beams 2a, . . . 2n are synthesized, and a reflectivity variation curve in flat trapezoidal form is obtained.

In the above embodiment, description has been given on a case where reflectivity is varied with respect to film thickness when the wavelength of the light beam is different. As shown in FIG. 18, it is known that, when an incident angle θ of the laser beam 2 to the substrate 5 is increased, the polarizing state of the laser beam 2 exerts influence on the reflectivity.

Now, description will be given on a tenth embodiment referring to FIG. 22.

Figure 22:
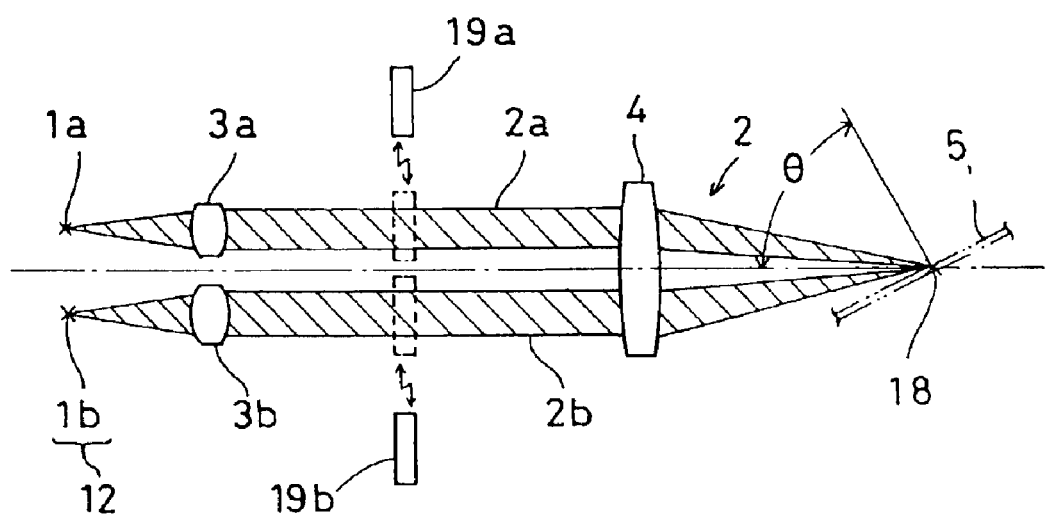
FIG. 22 is a drawing to explain a projecting optical system of a surface inspection system of a tenth embodiment of the present invention.

FIG. 22 is a schematical drawing of a projecting optical system 7 of the tenth embodiment of the invention. In the figure, the same component as shown in FIG. 18 is referred by the same symbol, and detailed description is not given here.

Light emitting sources 1a and 1b can independently control the light emitting condition. Laser beams 2a and 2b from the light emitting sources 1a and 1b are turned to parallel beams independently by collimator lenses 3a and 3b respectively and are converged and projected to the surface of the substrate 5 by a single image forming lens 4. Each of optical axes of the collimator lenses 3a and 3b is in parallel to an optical axis of the image forming lens 4. The laser beams 2a and 2b emitted from the light emitting sources 1a and 1b are converged to the same projecting point 18 by the image forming lens 4.

Polarizing members 19a and 19b are removably arranged respectively on optical axes of the laser beams 2a and 2b. The wavelengths of the laser beams 2a and 2b emitted from the light emitting sources 1a and 1b may be the same or different from each other. In the following, description is given by assuming that the wavelengths are the same. It is also assumed that the incident angle θ of the laser beam 2 to the substrate 5 is an angle, at which polarizing state of the laser beam 2 is reflected in the reflectivity.

As the polarizing member, a polarizing plate, a ½λ plate, ¼λ plate, a polarization canceling plate (to turn polarized light to random polarization), etc. may be used.

Figure 19:
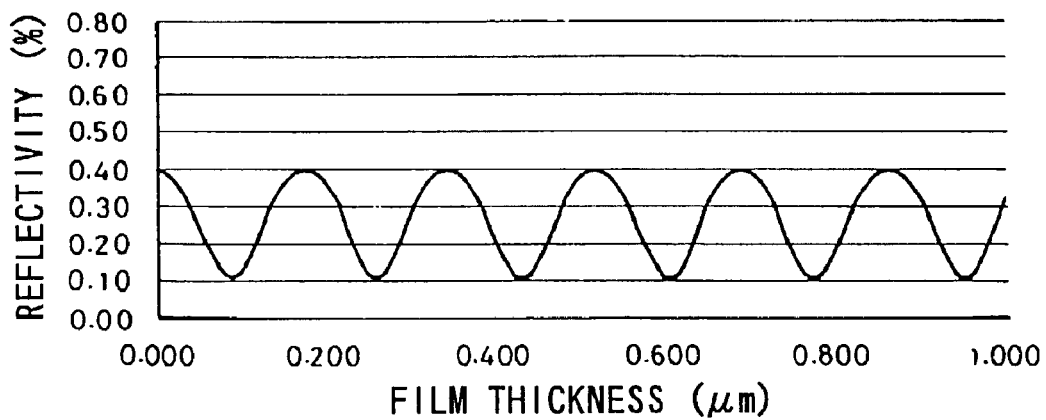
FIG. 19 is a diagram showing the relation between the change of film thickness and reflectivity when a laser beam of a single wavelength is projected to a surface of a substrate.
Figure 20:
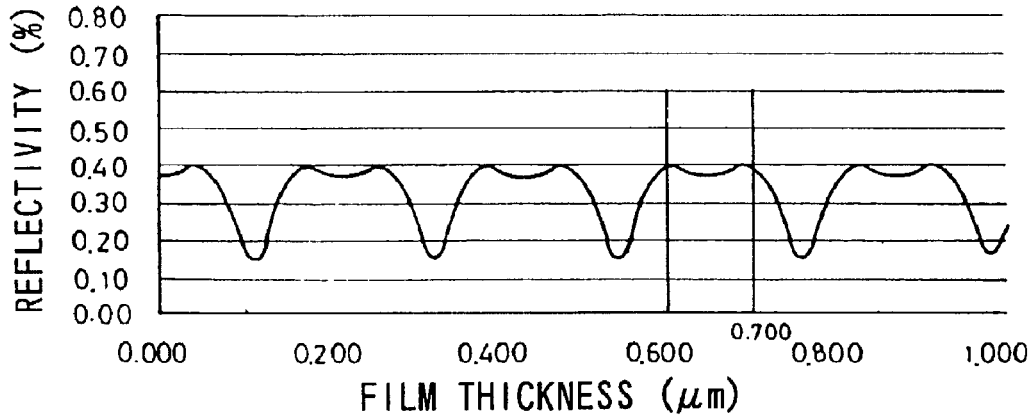
FIG. 20 is a diagram showing the relation between the change of film thickness and reflectivity when laser beams of single wavelength with different polarization are projected to the surface of the substrate.

In FIG. 22, for instance, when the polarizing member 19a is placed only to the optical axis of the laser beam 2a, polarization state of the laser beam 2a is changed from that of the laser beam 2b. For this reason, difference occurs in the reflectivity variation curve with respect to the change of film thickness between the laser beam 2a and the laser beam 2b as shown in FIG. 19. In the synthesized reflectivity variation curve of the laser beams 2a and 2b, peak values are in flat form between 0.6 μm and 0.7 μm in film thickness.

In the tenth embodiment, even when film thickness is varied, the scattered reflection light due to a foreign object or flaw is stable, and detection accuracy is stable and is not changed.

By selecting the polarizing plate, the ½λ plate, the ¼λ plate, or the polarization canceling plate, the polarization state of the laser beam can be changed, and the reflectivity variation curve is also changed. Therefore, by adequately selecting the polarizing members 19a and 19b, which are placed on the optical axes of the laser beams 2a and 2b, it is possible to adjust the reflectivity variation curve of the laser beams 2a and 2b.

It is needless to say that, when wavelengths of the laser beams 2a and 2b are changed, the reflectivity variation curve of the laser beams 2a and 2b is changed. By adequately selecting wavelength and polarization state of the laser beams, which are the factors to change the reflectivity variation curve, the range to adjust the reflectivity variation curve is widened, and it is possible to achieve the optimal reflectivity variation curve.

Figure 23:
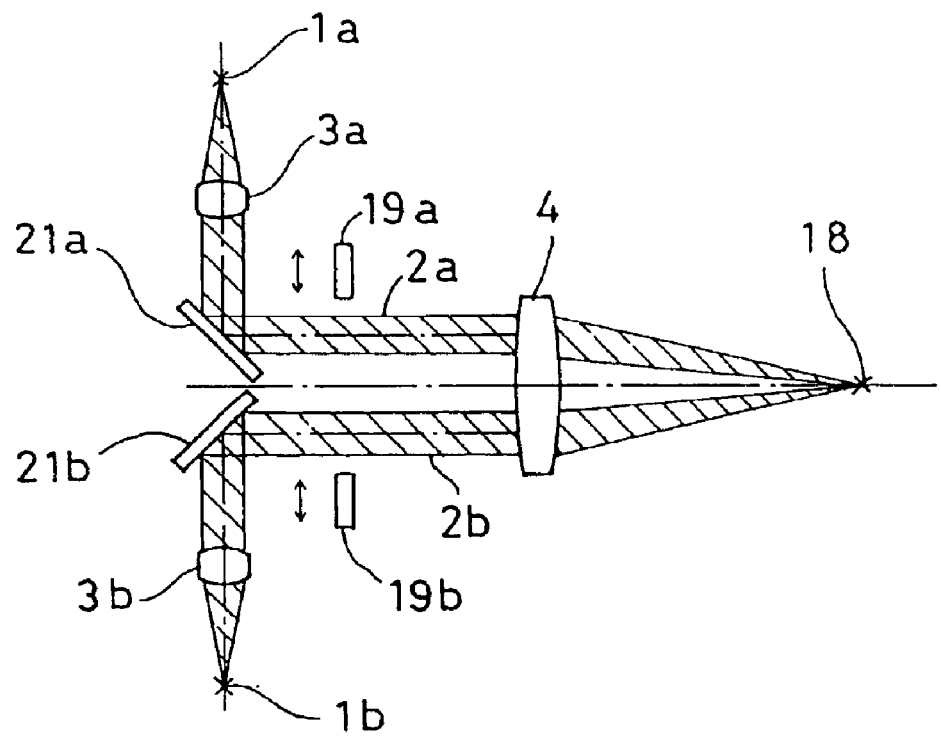
FIG. 23 is a drawing to explain a projecting optical system of a surface inspection system of an eleventh embodiment of the present invention.

FIG. 23 shows an eleventh embodiment of the invention. In this embodiment, the light emitting sources 1a and 1b are provided at positions separated from each other, and the laser beams are mixed.

A light emitting source 1a and a collimator lens 3a arranged at a position to match the light emitting source 1a are provided at positions crossing with respect to an optical axis of an image forming lens 4, for example, along an optical axis running perpendicularly to the optical axis of the image forming lens 4. The laser beam 2a emitted from the light emitting source 1a is reflected in a direction parallel to the optical axis of the image forming lens 4 by a reflection mirror 21a and is guided toward the image forming lens 4.

A light emitting source 1b and a collimator lens 3b are provided in similar arrangement. A laser beam 2b emitted from the light emitting source 1b is reflected by a reflection mirror 21b, runs in parallel to the optical axis of the image forming lens 4, and enters the image forming lens 4.

By the image forming lens 4, the laser beams 2a and 2b emitted from the light emitting sources 1a and 1b are converged to a projecting point 18.

When there are three or more light emitting sources 1 in the above eleventh embodiment, the light emitting sources 1 and the collimator lenses 3 should be arranged on a radial line with its center on the optical axis of the image forming lens 4.

In the eleventh embodiment as described above, if wavelengths of the laser beams emitted from the light emitting sources 1a and 1b are changed or polarizing members 19a and 19b are removed from or placed on the optical axes of the laser beams 2a and 2b, a reflectivity variation curve similar to the embodiment as given above can be obtained, and it is possible to achieve the optimal reflectivity variation curve.

Figure 24:
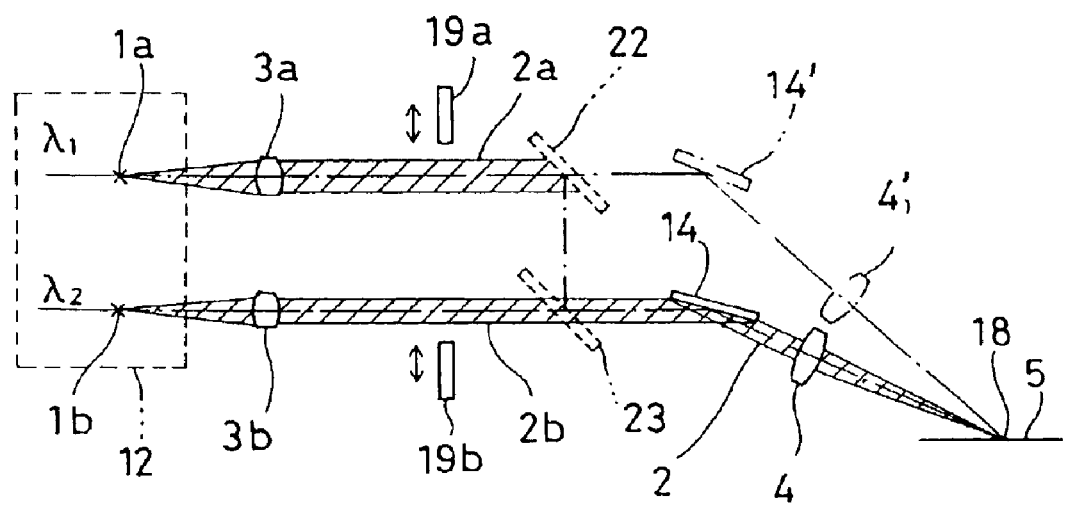
FIG. 24 is a drawing to explain a projecting optical system of a surface inspection system of a twelfth embodiment of the present invention.

FIG. 24 shows a twelfth embodiment. In this embodiment, light emitting sources 1a and 1b are provided at positions separated from each other as in the eleventh embodiment, and the laser beams 2a and 2b are mixed.

A light source unit 12 has two sets of light emitting sources 1a and 1b provided at separate positions. The light emitting sources 1a and 1b can independently control the light emitting condition and emit laser beams 2a and 2b having different wavelengths λ1 and λ2 respectively.

The laser beams 2a and 2b from the light emitting sources 1a and 1b are turned independently to parallel beams by collimator lenses 3a and 3b respectively. A reflection mirror 22 is arranged on the optical axis of the laser beam 2a, and a half-mirror 23 is provided at an intersection of the optical axis of the reflection light from the reflection mirror 22 and the optical axis of the collimator lens 3b.

The laser beam 2a is reflected by the reflection mirror 22 and the half-mirror 23 and it joins the laser beam 2b, which has passed through the half-mirror 23. Then, the laser beams are converged and projected to the projecting point 18 of the substrate 5 on the optical axis of the image forming lens 4.

In the twelfth embodiment as described above, if the wavelengths of the laser beams emitted from the light emitting sources 1a and 1b are changed and if polarizing members 19a and 19b are removed from or placed on the optical axes of the laser beams 2a and 2b respectively, a reflectivity variation curve as in the embodiment given above can be obtained, and the optimal reflectivity variation curve can be obtained.

In the twelfth embodiment as described above, it may be designed in such manner that the reflection mirror 22 and the half-mirror 23 are not used, and that the laser beam 2a from the light emitting source 1a is converged and projected directly to the projecting point 18 by a deflection optical member 14' and an image forming lens 4', and the laser beams 2a and 2b may be mixed at the projecting point 18. In this case, the laser beams 2a and 2b have different incident angles with respect to the substrate 5, and reflection characteristics are also influenced by the incident angle. Thus, by switching over the optical path of the laser beams 2a and 2b, different reflection characteristics can be obtained.

Figure 25:
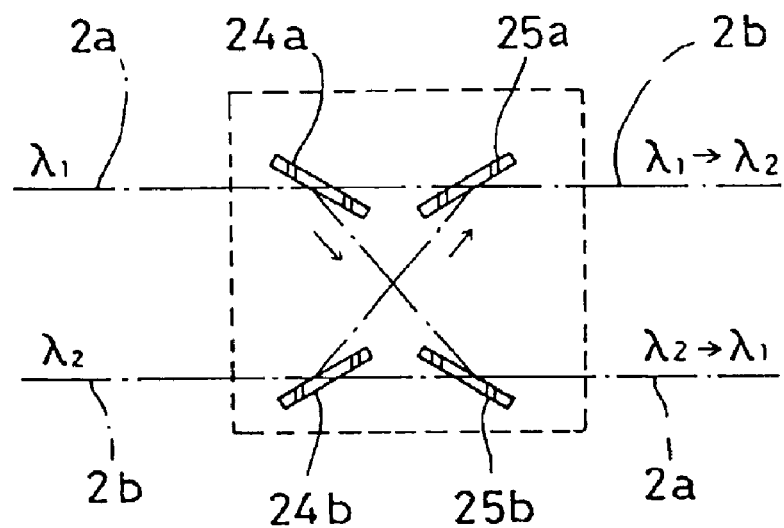
FIG. 25 is a drawing to explain an example of an optical path switching means in the twelfth embodiment of the invention.

FIG. 25 shows an example of an optical path switching means.

Reflection mirrors 24a and 25a are integrally and removably arranged on the optical axis of the laser beam 2a and reflection mirrors 24b and 25b are integrally and removably arranged on the optical axis of the laser beam 2b. When the reflection mirrors 24a and 25a and the reflection mirrors 24b and 25b are placed at the positions, the laser beam 2a is reflected by the reflection mirrors 24a and 25b and joins the optical axis of the laser beam 2b before the switching. The laser beam 2b is reflected by the reflection mirrors 24b and 25a and joins the optical axis of the laser beam 2a before the switching. Thus, each of the optical path is changed.

Figure 26:
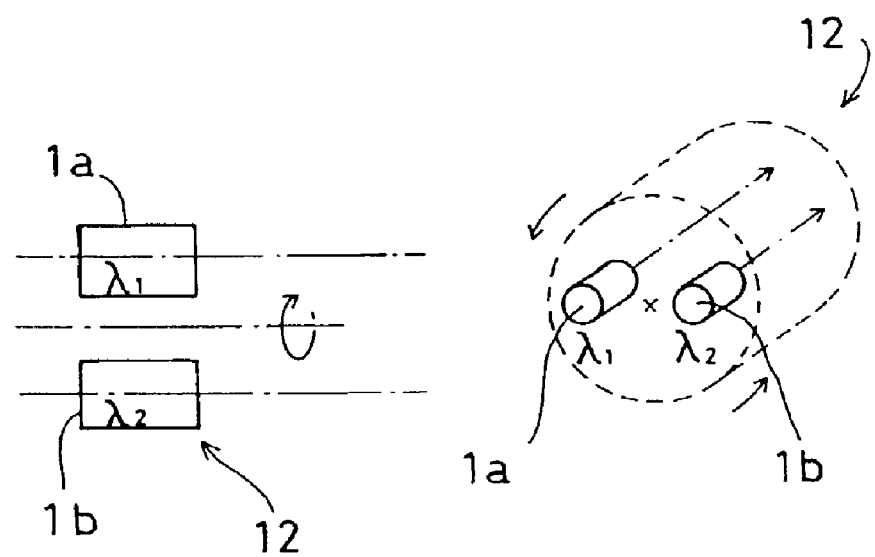
FIG. 26(A) and FIG. 26(B) each represents another example of the optical path switching means in the twelfth embodiment.
Figure 27:
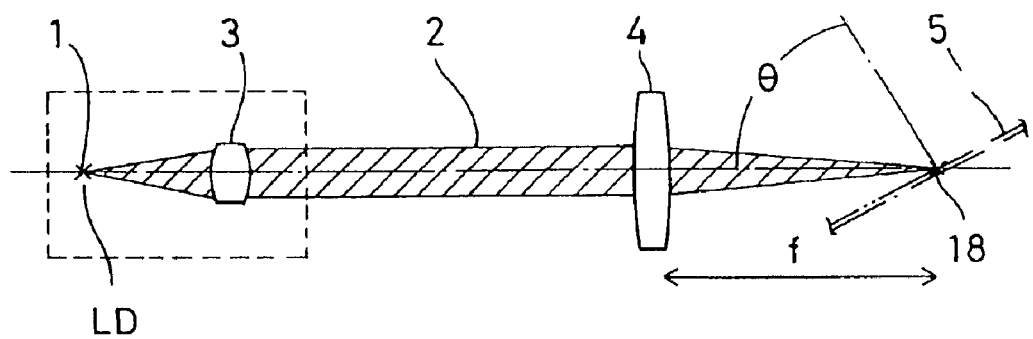
FIG. 27 is a drawing to explain a projecting optical system of a conventional type surface inspection system.
Figure 28:
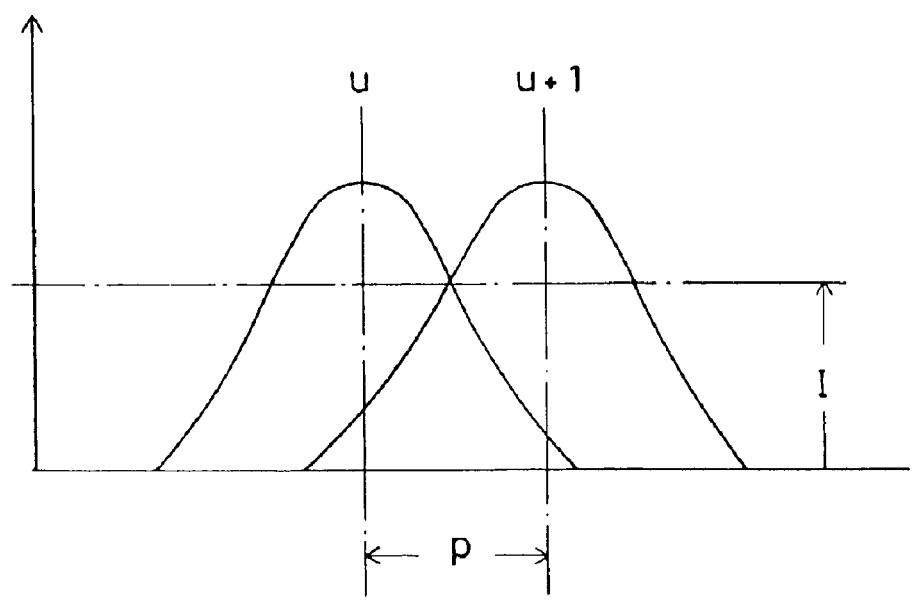
FIG. 28 is a diagram showing the relation between projected light intensity and scanning pitch in the conventional type surface inspection system.

FIG. 26(A) and FIG. 26(B) each represents another example of the optical path switching means.

In this another optical path switching means, the light emitting sources 1a and 1b can be integrally rotated. By rotating the light emitting sources 1a and 1b at an angle of 180°, the optical path is switched over.

In the embodiment shown in FIG. 21, a plurality of light emitting sources 1 are arranged along a straight line. The light emitting sources may be arranged in as many columns as required, and a plurality of light emitting sources 1 may be arranged in form of matrix.

In the arrangement in form of matrix, light intensity at the projecting point can be adjusted as given below although it is not particularly shown in the figure. Now, description will be given referring to FIG. 21.

That is, for each column, wavelength is changed for the light emitting source 1. Further, a polarizing member 19 is placed or removed as appropriate. Reflectivity of each laser beam is synthesized for the first column so that the reflectivity variation curve of flat trapezoidal form can be obtained. Next, for the second column and after, it is turned to such state that reflectivity variation curve similar to that of the first column can be obtained. Optical axes of the collimator lenses 3 arranged to match each of the light emitting sources are made parallel to the optical axis of the image forming lens 4.

Under this condition, all of the laser beams 2 are converged and projected to the projecting point 18. For each column, a reflectivity variation curve in flat trapezoidal form can be obtained. Further, light intensity of each column is summed up as many times as the columns, and the amount of the scattered reflection light is increased.

When the projected light intensity is increased, the detection accuracy is improved. When a plurality of light emitting sources 1 are arranged in form of matrix, stability of inspection accuracy with respect to the change of film thickness is improved in the surface inspection system, and improvement of inspection accuracy is achieved.

Further, this is also effective to a case where a blue laser diode is used as the laser beam 2 and sufficient light amount cannot be obtained by a single laser beam.

The arrangement of the plurality of light emitting sources is not limited to the form of matrix, and it may be in circular arrangement or other arrangement. It is essential that wavelength, polarization state and light intensity of each light emitting source should be adjusted so that a flat reflectivity variation curve is obtained.

The present invention provides a surface inspection system for projecting a laser beam to a surface of a substrate and for detecting a foreign object by detecting scattered reflection light of the laser beam, comprising a light source unit having a plurality of light emitting sources for emitting the laser beams, and a projecting optical system for projecting the laser beam from each of the light emitting sources to the surface of the substrate so that reflection characteristics on the substrate surface differ from each other. As a result, it is possible to avoid the scattered reflection light from being influenced by the type of film or by film thickness on the substrate surface, and the inspection can be performed in stable manner and with high accuracy.

What is claimed is:

1. A surface inspection system for projecting a laser beam to a surface of a substrate and for detecting a foreign object by detecting scattered reflection light of the laser beam, comprising a light source unit having a plurality of light emitting sources for emitting the laser beams, and a projecting optical system having an image forming lens having an optical axis, and for projecting the laser beam from each of said light emitting sources to said surface of the substrate, wherein the laser beams enter said image forming lens in such a manner that at least one of the laser beams is tilted with respect to said optical axis of said image forming lens.

2. A surface inspection system according to claim 1, further comprising optical axis tilting means for tilting the optical axis of the laser beam from said light emitting sources with respect to said optical axis of said image forming lens.

3. A surface inspection system according to claim 1, wherein the laser beam from at least one light emitting source is entered at a predetermined angle with respect to the optical axis of said image forming lens.

4. A surface inspection system according to claim 1, wherein at least one of the laser beams from light emitting sources forms an image at a position deviated from said optical axis of said image forming lens.

5. A surface inspection system according to claim 3, wherein an optical axis tilting means for tilting an optical axis is provided on at least one optical axis of the light beams entering said image forming lens from said light emitting sources.

6. A surface inspection system according to claim 4, wherein the image forming positions are deviated in a direction crossing a scanning direction.

7. A surface inspection system according to claim 1, wherein said plurality of light emitting sources emit light beams with different wavelengths.

8. A surface inspection system according to one of claims 1, 2, or 7, wherein said light emitting sources are arranged in the form of a matrix and wherein the laser beams from said light emitting sources belonging to at least one row or at least one column of said matrix are tilted.

9. A surface inspection system according to one of claim 1, wherein said plurality of light emitting sources can independently change the light emitting condition.

10. A surface inspection system according to one of claim 2 or 5, wherein said optical axis tilting means is a wedge prism.

11. A surface inspection system according to one of claim 2 or 5, wherein said optical axis tilting means is a reflection mirror.

* * * * *